Sept. 3, 1974 TOSHIO ISHII Plant Pat. 3,606
GARDENIA PLANT
Filed March 8, 1973
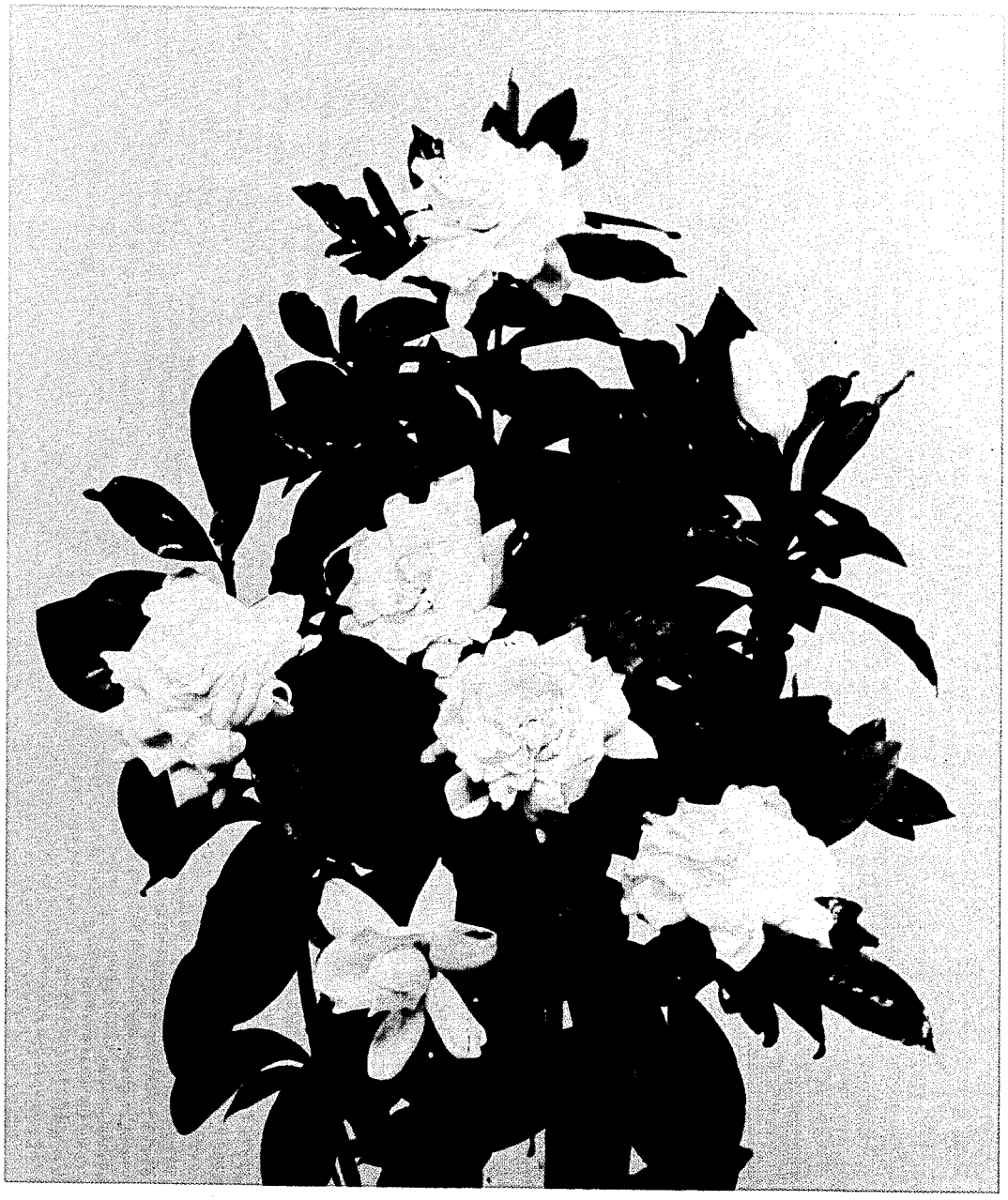

United States Patent Office

Plant Pat. 3,606
Patented Sept. 3, 1974

3,606

GARDENIA PLANT

Toshio Ishii, Gardena, Calif., assignor to Armstrong Nurseries, Inc., Ontario, Calif.

Filed Mar. 8, 1973, Ser. No. 339,189
Int. Cl. A01h *5/00*
U.S. Cl. Plt.—54 1 Claim

ABSTRACT OF THE DISCLOSURE

A new variety of Gardenia being a sport of the jasminoides species, having highly spicy and sweet-scented blooms which open on the bush a true white, become cream colored after a few days, and then turn golden yellow within eight days after the corolla first opens. Cut flowers change color more rapidly, becoming golden yellow in four days and lasting a week or slightly less. The bloom has no pistils, anthers or stamens. The plant is vigorous, bushy, upright-spreading and abundantly covered with glossy dark green foliage.

This invention relates to a variety of Gardenia of the jasminoides species. Plants are grown primarily for the production of cut flowers, and also for garden decoration.

The new variety is a sport found in a garden in Hawaii, growing on a shrub of the variety known as "Mystery." Propagating material was brought from Hawaii to Gardena, California, where the new variety was first asexually reproduced from cuttings.

The description which follows relates to the same variety, grown in 5-gallon containers in a greenhouse located in Ontario, California. The new cultivar holds its characteristics well through successive propagations from cuttings.

This new variety differs from its parent, Gardenia jasminoides "Mystery," when grown under comparable conditions, in several respects. Insofar as the flower is concerned, the buds of the new cultivar are significantly broader in relation to their length than are the buds of "Mystery"; there are many more petals (from 35 to 45, as compared to 21 to 25 on the bloom of the parent); and the petals of the new cultivar curve outward along their margins, whereas the petals of "Mystery" remain cupped, with the margins curved inward. The new cultivar displays no sexual reproductive organs at all, whereas "Mystery" possesses both male and female reproductive organs, with the anthers showing clearly in the opening flowers.

The flowers of the new variety preserve their quality and form unblemished for as long as thirteen days on the bush, whereas the blooms of "Mystery" have lost their crispness and form and have become brown and unsightly after only about eight days. The blooms of "Mystery" do not pass through the color transitions (white to cream to golden yellow) which apply to the new cultivar, but remain white until they begin to discolor.

As to the plant, the new cultivar has a more upright habit of growth than its parent, with more branching, giving a compact effect, and although its stems are similar in appearance, they bend less. The leaves are similar in shape to those of "Mystery," but they are flatter and less crinkled. Furthermore, the leaves are narrower in proportion to their length than are the leaves of the parent.

As to behavioral differences, it is noted that the new cultivar is distinctly more resistant to iron chlorosis than the parent plant, and also manifests a somewhat better resistance to aphids and mites.

If the present cultivar be compared with another gardenia which likewise passes through a yellow phase, we may consider the variety known as the "Belmont" gardenia, which has significantly fewer petals (18 to 26) plus a few

(10) tightly whorled smaller petals, as compared to the new variety which has from 35 to 45 petals and quite a number of inconspicuous tightly whorled undeveloped petals in the center of the bloom. The new cultivar has neither pistils nor anthers, whereas Belmont usually has two pollen-bearing anthers or antherlike structures. When the bloom of the new cultivar is fully open and in its prime, it has a coloration between creamy pale yellow (lighter than Brilliant Yellow, 2.5Y9/9) and Vivid Yellow, 2.5Y8/12.* With the Belmont gardenia, the flower color "in its prime" is "pure white, no yellow or green tints being visible", to paraphrase the description given in the patent for this variety.

The branches and main stems of the new cultivar are brown in color, whereas branches and main stems of Belmont are green.

The accompanying illustration shows the plant in full color from opening bud to mature flower.

In Southern California, the plant manifests two major blooming periods, the first from mid-April to the end of May, and the second from early July to mid-August. Some light blooming may occur during June and also early in September. The quantity of bloom is ample.

THE BLOOM

The bud has a corolla from about 1¾" to 2¼" long, which is very plump, prior to opening, and ⅝" to ¾" in width. It is supported on a peduncle which is long and heavy with a from 5 to 7 lobed limb. The color is near Moderate Yellow Green, 7.5GY5/7. As the first petals open, the color is near pure white on the inside with near Strong Yellow Green, 2.5GY7/10, on the outside surface of the outer petals, and a lighter shade of the same color along the inner margins of the outer petals.

The flowers are borne singly, and range from 3" to 4" in diameter when fully open. They have a very sweet fragrance which is spicy and penetrating. There are from 35 to 45 petals, arranged in 6 or 7 rows. Of these, the outer petals are from 1½" to 1¾" long and are obovate in shape. The inner petals become progressively smaller towards the center, and their shape becomes broadly obovate to nearly round. The centermost petals remain small, green, and undeveloped, but they are inconspicuous, even when the bloom is fully open. The petal texture is very heavy, being velvety on the inner surface and waxy on the outer surface.

The form of the bloom is high-centered at first, becoming flat with a raised center. The petals, at first, are very tightly whorled, becoming at maturity fully open, with margins reflexed outward. The petals overlap in the form of a semi-flat layered rosette when the flower is fully open.

The color, as the corolla begins to open, is waxy white, which likewise is the color of the newly opened flower. On the outer surface of the outer petals, where exposed to sunlight, the pure white petals have some markings of near Strong Yellow Green, 2.5GY7/10. This also appears lightly along the inner surface of the petal margins which developed on the outer surface of the unopened bud. Within two to four days the bloom is near creamy pale yellow, between off-white and Brilliant Yellow, 2.5Y9/9. Within four days the bloom has become cream colored, after which it gradually turns a rich golden yellow within eight days. The bloom retains its color and its attractive form for several additional days, each individual flower persisting for from eleven to thirteen days on the bush, in Southern California in the months of May and June. When the flowers have been open four to eleven days, the general color of the bloom is near Vivid Yellow, 2.5Y8/12,

*Color names with initial capital letters represent color values based on the Nickerson Color Fan (Munsell).

and the flower remains fresh looking througout this period without blemish or browning of the petal margins; thereafter petals begin at the margins to turn brown and shrivel, until the entire flower, which after its demise often persists several weeks on the bush, has browned, shriveled and died. Cut flowers kept at living room temperatures and conditions will maintain their form and fragrance for from five to seven days, passing more rapidly through the color transition and becoming golden yellow in four days.

REPRODUCTIVE ORGANS

Flowers of this new gardenia have no stamens or anthers, and no pistils.

THE PLANT

Growth: An evergreen shrub, vigorous and strong, well covered with foliage.

Habit: Bushy, upright-spreading, and much-branched.

Stems: Brown on hard wood, strong, sturdy, sometimes bending slightly.

Foliage: Leaves are opposite or occur in threes.

Leaf size: 3" to 5½" long, 1½" to 1¾" wide.

Leaf shape: Lanceolate to elliptic with a cuspidate apex and acute base.

Leaf texture: Heavy, with leaf veins giving a slightly crinkled effect.

Leaf color: Very dark green with soft lighter shading on the underside and radiant veining showing on the underside. Very glossy on the upper surface and somewhat dull on the underside, except for veins.

The upper surface of the mature foliage is between Moderate Olive Green, 5GY4/3, and Grayish Olive Green, 5GY3/2, the under surface being near Moderate Yellow Green, 5GY5/6.

The upper surface of the young foliage is between Strong Yellow Green, 5GY6/8, and Strong Yellow Green, 7.5GY6/8, with the under surface being between Strong Yellow Green, 5GY7/10, and Strong Yellow Green, 5GY6/8.

I claim:

1. A new and distinct variety of gardenia plant substantially as herein shown and described, being especially characterized in the fact that its blooms do not display anthers, stamens, or pistils, and in that the blooms change from pure white as the blossom opens to a cream color within three or four days, and then change to a deep golden yellow within eight days after opening, the blooms holding their form, texture, color and fragrance on the bush substantially unimpaired, in Southern California, until the twelfth or thirteenth day, or for from five to seven days if cut and kept at room temperature.

No references cited.

ROBERT E. BAGWILL, Primary Examiner